(12) United States Patent
Fink

(10) Patent No.: US 12,263,022 B1
(45) Date of Patent: Apr. 1, 2025

(54) MEDICAL WASTE GRINDING AND SEPARATION SYSTEM WITH PATHOGEN NEUTRALIZATION

(71) Applicant: Sharp's Salvation LLC, Amarillo, TX (US)

(72) Inventor: David Fink, Amarillo, TX (US)

( * ) Notice: Subject to any disclaimer, the term of this patent is extended or adjusted under 35 U.S.C. 154(b) by 0 days.

(21) Appl. No.: 18/810,098

(22) Filed: Aug. 20, 2024

(51) Int. Cl.
*A61B 50/30* (2016.01)
*A61B 50/36* (2016.01)

(52) U.S. Cl.
CPC .... *A61B 50/3001* (2016.02); *A61B 2050/364* (2016.02)

(58) Field of Classification Search
CPC ............ A61B 50/3001; A61B 2050/364
USPC ............................................ 206/366
See application file for complete search history.

(56) References Cited

U.S. PATENT DOCUMENTS

| | | | |
|---|---|---|---|
| 3,404,593 A | 10/1968 | Arcarese | |
| 3,796,359 A | 3/1974 | Dick | |
| 4,275,628 A | 6/1981 | Greenhouse | |
| 4,404,881 A | 9/1983 | Hanifl | |
| 4,494,652 A | 1/1985 | Nelson | |
| 4,553,687 A | 11/1985 | Harkins | |
| 4,786,280 A | 11/1988 | Maeda | |
| 4,867,309 A | 9/1989 | Germain | |
| 4,869,366 A | 9/1989 | Bruno | |
| 5,183,156 A | 2/1993 | Bruno | |
| 2013/0306507 A1* | 11/2013 | Sichau | A61B 50/36 206/366 |
| 2015/0164590 A1* | 6/2015 | Sakihama | A61M 5/3205 206/366 |
| 2019/0183737 A1* | 6/2019 | Valerino, Sr. | B65G 51/26 |

* cited by examiner

*Primary Examiner* — Jacob K Ackun
(74) *Attorney, Agent, or Firm* — Shannon Warren

(57) ABSTRACT

A medical waste grinding and separation system configured to safely neutralize and dispose of a portion of a medical sharp. The medical waste grinding and separation system comprises an outer casing, a sharps aperture, a grinding head, a rotary grinding tool motor, a debris reservoir, a power system, a debris channel, a drive shaft the grinding head comprises a grinding surface. The grinding surface comprises a portion of the grinding head being closest to the sharps aperture. The outer casing 200 forms the main structural body of the system, housing the internal components the grinding head and the rotary grinding tool motor is aligned with one another and the sharps aperture. The grinding head is configured to grind down the tip of a syringe when it is inserted into the aperture. The grinding head is driven by the rotary grinding tool motor.

20 Claims, 10 Drawing Sheets

MEDICAL WASTE GRINDING AND SEPARATION SYSTEM WITH PATHOGEN NEUTRALIZATION

CROSS-REFERENCE TO RELATED APPLICATIONS

Not applicable.

STATEMENT REGARDING FEDERALLY SPONSORED RESEARCH OR DEVELOPMENT (IF APPLICABLE

Not applicable.

REFERENCE TO SEQUENCE LISTING, A TABLE, OR A COMPUTER PROGRAM LISTING COMPACT DISC APPENDIX (IF APPLICABLE

Not applicable.

BACKGROUND OF THE INVENTION

Handling medical waste in medical contexts is both expensive and hazardous. Traditional methods rely on robust containers known as sharps containers to capture and store medical waste for disposal in landfills. While effective in containment, this method incurs significant costs for both the containers and the frequent replacement services, especially in hospital and clinic settings. Each sharp container can cost between $5 and $10, with additional service charges for regular collection and disposal, which can accumulate quickly due to the high usage frequency in medical environments.

Medical waste, particularly sharps such as needles and syringes, poses serious risks due to their potential to cause injury and transmit infections. Current disposal techniques include the use of autoclaves, which heat materials to 285° F. to kill pathogens. However, this process is energy-intensive and requires significant infrastructure.

An alternative approach involves destroying the needle portion of syringes using a grinder. This method not only physically destroys the needle but also generates heat during grinding, effectively sterilizing the needle by killing pathogens. Additionally, it facilitates the separation of recyclable plastics from the dangerous metal components, offering an environmentally friendly disposal option.

Despite these advantages, existing grinder systems can be improved. The need for a portable, efficient, and safe disposal system is clear, especially in the context of reducing costs and enhancing safety in medical waste handling.

The average hospital incurs substantial expenses due to the cost of sharps containers and their associated service contracts. Moreover, improper handling and disposal of medical sharps can result in injuries and exposure to bloodborne pathogens for healthcare workers, necessitating better solutions.

In response to these challenges, the present invention provides an improved medical waste grinding and separation system. This system is designed to be portable and efficient, equipped with sensors to detect the material being ground, ensuring the grinding process stops when non-metal components are detected. This feature prevents unnecessary wear on the grinding tool and reduces contamination risks.

The system includes a removable debris container with a drawer or latch for easy disposal, a cover to prevent the escape of grinding dust, and a battery-operated design for portability. Additionally, it is capable of handling glass medical waste, such as vials and bottles commonly used in medical settings, further enhancing its utility and efficiency in medical waste management.

These prior art references are known to the inventor but are not seen as relevant to the current claims: U.S. Pat. Nos. 4,867,309, 4,494,652, 3,796,359, 4,553,687, 4,275,628, 4,404,881, 3,404,593, 4,869,366, 5,183,156, and 4,786,280.

BRIEF SUMMARY OF THE INVENTION

A medical waste grinding and separation system 100 configured to safely neutralize and dispose of a portion of a medical sharp. Said medical waste grinding and separation system 100 comprises an outer casing 200, a sharps aperture 204, a grinding head 300, a rotary grinding tool motor 302, a debris reservoir 306, a power system 308, a debris channel 402, a drive shaft 408 said grinding head 300 comprises a grinding surface 404. Said grinding surface 404 comprises a portion of said grinding head 300 being closest to said sharps aperture 204. Said outer casing 200 forms the main structural body of the system, housing the internal components said grinding head 300 and said rotary grinding tool motor 302 is aligned with one another and said sharps aperture 204. Said grinding head 300 is configured to grind down the tip of a syringe when it is inserted into the aperture. Said grinding head 300 is driven by said rotary grinding tool motor 302. Said debris reservoir 306 comprises a compartment within said medical waste grinding and separation system 100 that collects and stores the ground debris produced by said grinding head 300. Said power system 308 is configured to provide the necessary electrical power to said medical waste grinding and separation system 100. Said debris channel 402 is positioned between said sharps aperture 204 and said debris reservoir 306. Said debris channel 402 directs debris from said grinding surface 404 of said grinding head 300 and into said debris reservoir 306. Accordingly, said debris channel 402 ensures that the debris is efficiently collected without scattering. Said grinding head 300 and said rotary grinding tool motor 302 are connected via said drive shaft 408. Medical waste grinding and separation system 100 further comprises an air compressor 310, and an air nozzle 412. Said air compressor 310 assists with the collection of debris by generating an airflow that helps direct the ground debris into said debris reservoir 306, maintaining a clean and efficient operation. Said air nozzle 412 is installed in a portion of said debris reservoir 306 and is connected to said air compressor 310 to pull air from said debris reservoir 306.

Said medical waste grinding and separation system 100 configured to safely neutralize and dispose of a portion of a medical sharp. Said medical waste grinding and separation system 100 comprises said outer casing 200, said sharps aperture 204, said grinding head 300, said rotary grinding tool motor 302, said debris reservoir 306, said power system 308, said debris channel 402, said drive shaft 408 said grinding head 300 comprises said grinding surface 404. Said grinding surface 404 comprises a portion of said grinding head 300 being closest to said sharps aperture 204. Said outer casing 200 forms the main structural body of the system, housing the internal components said grinding head 300 and said rotary grinding tool motor 302 is aligned with one another and said sharps aperture 204. Said grinding head 300 is configured to grind down the tip of a syringe when it is inserted into the aperture. Said grinding head 300 is driven by said rotary grinding tool motor 302. Said debris reservoir 306 comprises a compartment within said medical waste grinding and separation system 100 that collects and stores the ground debris produced by said grinding head 300. Said power system 308 is configured to provide the necessary electrical power to said medical waste grinding and separation system 100. Said debris channel 402 is positioned between said sharps aperture 204 and said debris reservoir 306. Said debris channel 402 directs debris from said grinding surface 404 of said grinding head 300 and into said debris reservoir 306. Accordingly, said debris channel 402 ensures that the debris is efficiently collected without scattering. Said grinding head 300 and said rotary grinding tool motor 302 are connected via said drive shaft 408.

A method of use 600 of said medical waste grinding and separation system 100 for safely neutralizing and disposing of a portion of a medical sharp. Said method of use 600 comprising ensuring said medical waste grinding and separation system 100 is properly supplied with power for said power system 308 and verifying that said debris reservoir 306 has sufficient space to collect debris, inserting a contaminated medical sharp into said sharps aperture 204, powering said rotary grinding tool motor 302, driving said grinding head 300 to grind the contaminated medical sharp, directing debris through said debris channel 402, collecting it in said debris reservoir 306, monitoring a grinding event and shutting down said rotary grinding tool motor 302 when completed, safely disposing of the collected debris according to medical waste disposal regulations. Wherein, said medical waste grinding and separation system 100 comprises said outer casing 200, said sharps aperture 204, said grinding head 300, said rotary grinding tool motor 302, said debris reservoir 306, said power system 308, said debris channel 402, said drive shaft 408 said grinding head 300 comprises said grinding surface 404. Said grinding surface 404 comprises a portion of said grinding head 300 being closest to said sharps aperture 204. Said outer casing 200 forms the main structural body of the system, housing the internal components said grinding head 300 and said rotary grinding tool motor 302 is aligned with one another and said sharps aperture 204. Said grinding head 300 is configured to grind down the tip of a syringe when it is inserted into the aperture. Said grinding head 300 is driven by said rotary grinding tool motor 302. Said debris reservoir 306 comprises a compartment within said medical waste grinding and separation system 100 that collects and stores the ground debris produced by said grinding head 300. Said power system 308 is configured to provide the necessary electrical power to said medical waste grinding and separation system 100. Said debris channel 402 is positioned between said sharps aperture 204 and said debris reservoir 306. Said debris channel 402 directs debris from said grinding surface 404 of said grinding head 300 and into said debris reservoir 306. Accordingly, said debris channel 402 ensures that the debris is efficiently collected without scattering. Said grinding head 300 and said rotary grinding tool motor 302 are connected via said drive shaft 408.

DETAILED DESCRIPTION OF THE INVENTION

The following description is presented to enable any person skilled in the art to make and use the invention as claimed and is provided in the context of the particular examples discussed below, variations of which will be readily apparent to those skilled in the art. In the interest of clarity, not all features of an actual implementation are described in this specification. It will be appreciated that in the development of any such actual implementation (as in any development project), design decisions must be made to achieve the designers' specific goals (e.g., compliance with system- and business-related constraints), and that these goals will vary from one implementation to another. It will also be appreciated that such development effort might be complex and time-consuming, but would nevertheless be a routine undertaking for those of ordinary skill in the field of the appropriate art having the benefit of this disclosure. Accordingly, the claims appended hereto are not intended to be limited by the disclosed embodiments, but are to be accorded their widest scope consistent with the principles and features disclosed herein.

Figure 1:
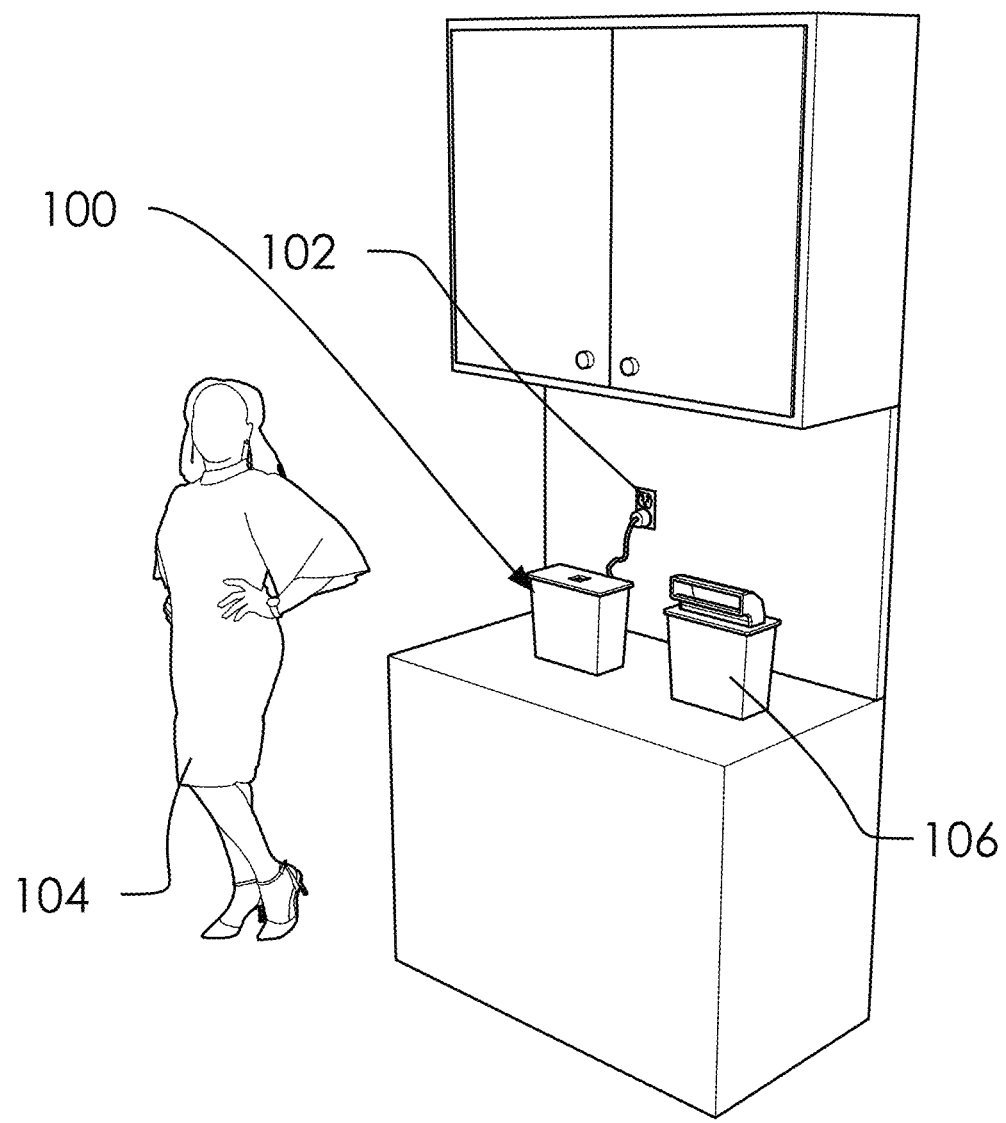
FIG. 1 illustrates a perspective overview of a medical waste grinding and separation system 100 in a medical setting 108.

FIG. 1 illustrates a perspective overview of a medical waste grinding and separation system 100 in a medical setting 108.

In one embodiment, said medical waste grinding and separation system 100 can be designed for use in a typical medical office environment. The system can be plugged into a wall outlet 102, allowing for easy integration into existing medical settings. Alternatively, the system can operate on batteries, providing flexibility and portability for use in various locations within the medical facility.

It is noted that said medical waste grinding and separation system 100 can be operated by a system user 104, who can be a medical professional or patient.

It is designed to neutralize a syringe that has been contaminated either through injection into a patient or by other contamination means, ensuring safe disposal of medical sharps.

For illustrative purposes, a sharps container 106 is shown. These containers, while necessary, pose significant risks due to the dangerous nature of their contents. They require careful handling and are typically serviced through contracts that involve regular collection and disposal. Sharps containers can be mounted to walls for convenience but always necessitate external service for proper disposal.

As discussed below, said medical waste grinding and separation system 100 offers a more efficient, safer, and potentially cost-effective solution for handling medical waste, reducing the reliance on external services and minimizing the risks associated with handling used sharps.

In one embodiment, said medical waste grinding and separation system 100 can be configured to safely neutralize and dispose of a portion of a medical sharp, as it is known in the art, which can include syringes.

Medical sharps are a broad category of medical instruments with sharp points or edges that are capable of puncturing or cutting skin. These typically include syringes, needles, scalpels, lancets, and other similar devices used in medical settings for various procedures. Handling medical sharps requires utmost care due to the significant risks they pose. Accidental injuries from medical sharps can lead to serious health hazards, including the transmission of blood-borne pathogens such as HIV, hepatitis B, and hepatitis C. Medical professionals are particularly at risk, as they routinely handle these instruments during patient care. Therefore, effective and safe disposal of medical sharps is crucial to protect healthcare workers and patients from potential infections and injuries. Said medical waste grinding and separation system 100 is designed to address these risks by neutralizing used syringes and other sharps, ensuring they are rendered safe for disposal and minimizing the reliance on traditional sharps containers that pose additional handling risks.

Figure 2:
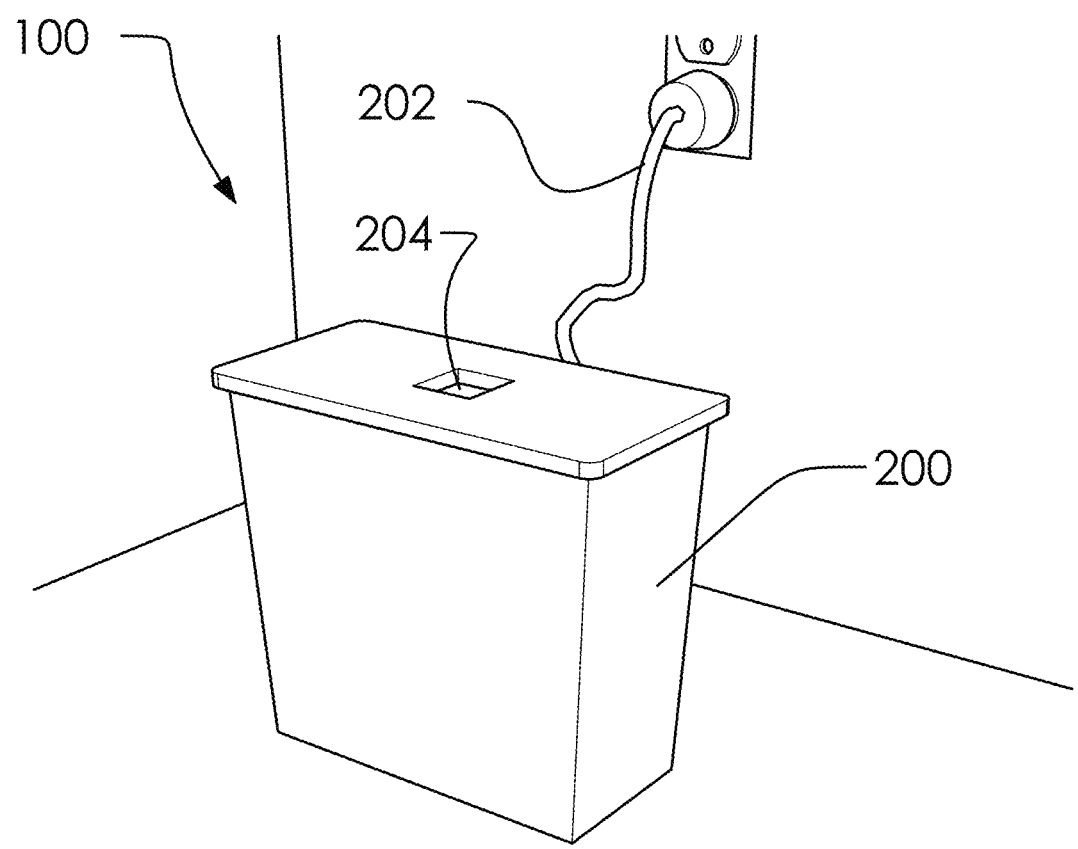
FIG. 2 illustrates a perspective overview of said medical waste grinding and separation system 100.

FIG. 2 illustrates a perspective overview of said medical waste grinding and separation system 100.

Said medical waste grinding and separation system 100 can comprise an outer casing 200, a plug 202, and a sharps aperture 204.

Wherein, said plug 202 can be connected to said wall outlet 102. This provides said medical waste grinding and separation system 100 with the necessary power to operate the grinding mechanism and associated components. Said outer casing 200 forms the main structural body of the system, housing the internal components and protecting them from external damage. The casing is designed to be durable and compact, making the system suitable for use in different environments, including being placed on a cabinet or mounted to a wall. Said sharps aperture 204 comprises an opening of said medical waste grinding and separation system 100 through which syringes can be inserted for grinding. Said sharps aperture 204 can be arranged in an upper portion of said medical waste grinding and separation system 100, as illustrated. Said sharps aperture 204 can be configured to ensure safe and easy insertion of syringes while preventing accidental exposure to the internal grinding mechanism.

Figure 3:
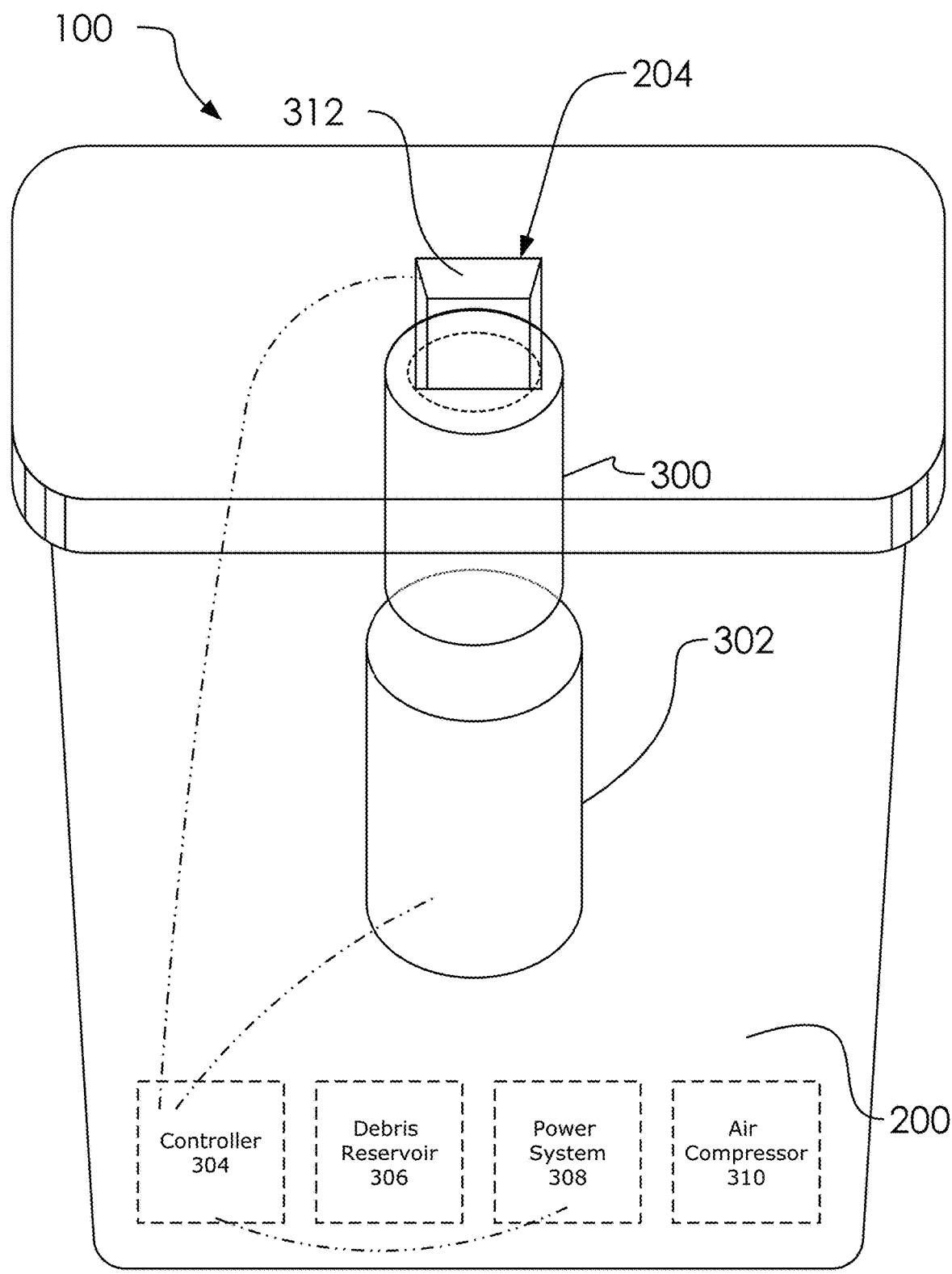
FIG. 3 illustrates a block diagram of said medical waste grinding and separation system 100 showing a portion of its internal components.

FIG. 3 illustrates a block diagram of said medical waste grinding and separation system 100 showing a portion of its internal components.

Said medical waste grinding and separation system 100 can further comprise a grinding head 300, a rotary grinding tool motor 302, a controller 304, a debris reservoir 306, a power system 308, an air compressor 310, and a sensor 312.

Said grinding head 300 and said rotary grinding tool motor 302 can be aligned with one another and said sharps aperture 204. In one embodiment, said grinding head 300 can be configured to grind down the tip of a syringe when it is inserted into the aperture. This process effectively neutralizes the syringe for safe disposal.

In one embodiment, said grinding head 300 can be driven by said rotary grinding tool motor 302. The motor provides the necessary power and torque to the grinding head, ensuring efficient and consistent grinding of medical sharps.

Further, said controller 304 can manage the operation of the various components within said medical waste grinding and separation system 100. For example, said controller 304 can control said rotary grinding tool motor 302 between active or inactive, as needed for the grinding process. Said controller 304 can coordinate the functions of the other components and maintains the overall operational efficiency and safety of the system.

Said debris reservoir 306 can comprise a compartment within said medical waste grinding and separation system 100 that collects and stores the ground debris produced by said grinding head 300. In one embodiment, said debris reservoir 306 can be removable, allowing for easy disposal and maintenance.

Said power system 308 can be configured to provide the necessary electrical power to said medical waste grinding and separation system 100. It can include a rechargeable battery system for portable operation or a direct power connection from a wall outlet. This dual-power option ensures that the system can be used flexibly in various medical settings.

Said air compressor 310 can assist with the collection of debris. The compressor generates airflow that helps direct the ground debris into said debris reservoir 306, maintaining a clean and efficient operation.

In one embodiment, an inner rim of said sharps aperture 204 can comprise said sensor 312. Wherein, said sensor 312 can be configured to detect the presence of an object inserted into said sharps aperture 204. Further, said sensor 312 can trigger the activation of said grinding head 300 and other system components, ensuring that the system operates only when necessary and enhancing user safety.

Said controller 304 can ensure said rotary grinding tool motor 302 drives said grinding head 300 when a medical sharp is inserted into said sharps aperture 204. Further, said sensor 312 can provide an additional layer of functionality by detecting the insertion of objects and activating the system as required.

Figure 4:
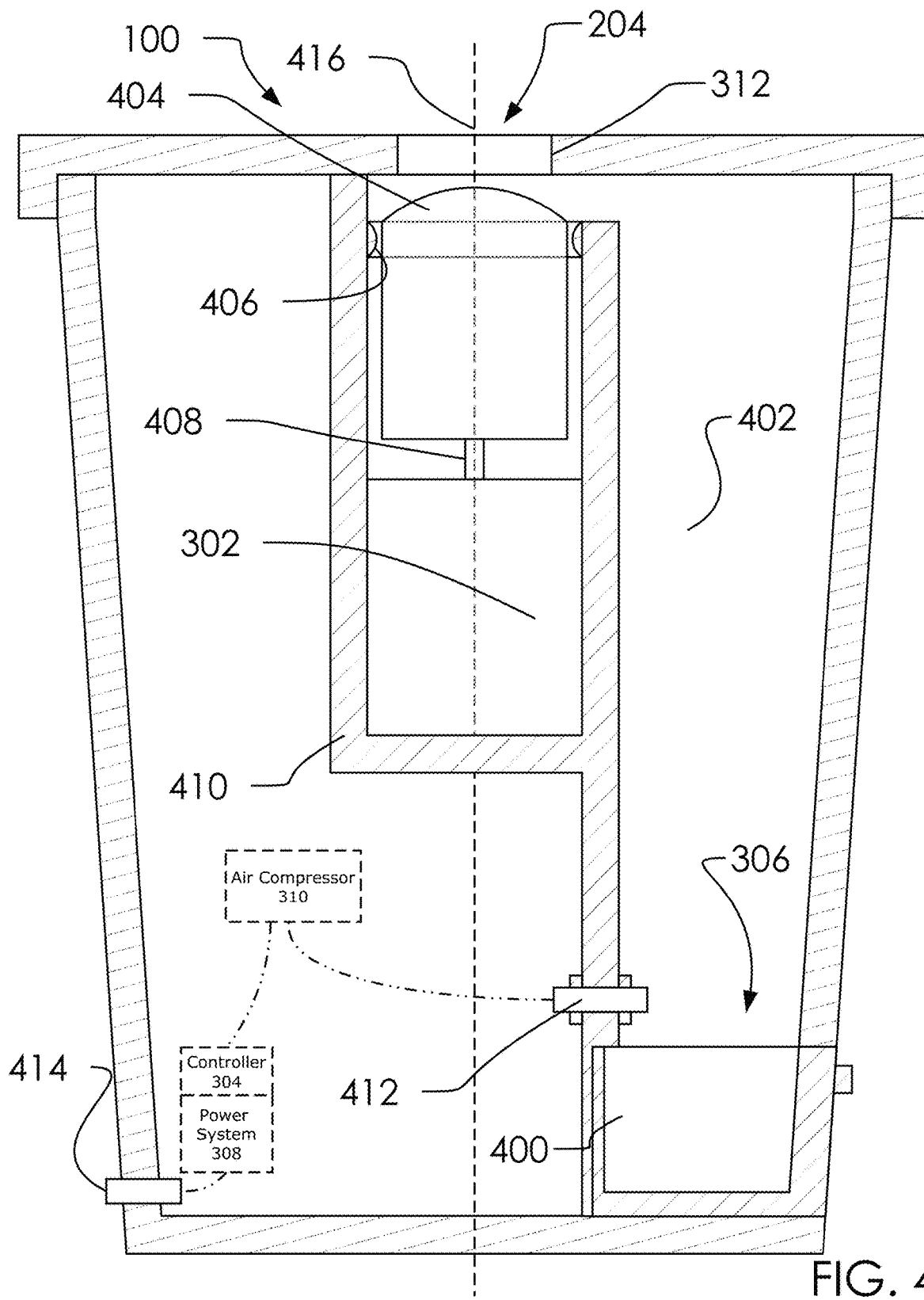
FIG. 4 illustrates an elevated cross-section side view of said medical waste grinding and separation system 100.

FIG. 4 illustrates an elevated cross-section side view of said medical waste grinding and separation system 100.

Said medical waste grinding and separation system 100 can further comprise a lower tray 400, a debris channel 402, a grinding surface 404, a blocking element 406, a drive shaft 408, a mounting bracket 410, an air nozzle 412, and a power port 414.

In one embodiment, said debris reservoir 306 can include said lower tray 400, which can be removed from said outer casing 200 to discard the collected debris. This design allows for easy and safe disposal of the debris accumulated within the container.

In one embodiment, said debris channel 402 can be positioned between said sharps aperture 204 and said debris reservoir 306. Wherein, said debris channel 402 directs debris from said grinding surface 404 of said grinding head 300 and into said debris reservoir 306. Accordingly, said debris channel 402 ensures that the debris is efficiently collected without scattering.

In one embodiment, said grinding head 300 and said rotary grinding tool motor 302 are connected via said drive shaft 408. In one embodiment, said grinding surface 404 can comprise a portion of said grinding head 300 being closest to said sharps aperture 204. Further, said grinding surface 404 can comprise a top portion of said grinding head 300.

Said blocking element 406 can be arranged around the perimeter of the grinding surface 404 to ensure that debris is directed into said debris reservoir 306 and does not fall into the chamber housing said grinding head 300 and said rotary grinding tool motor 302.

Said air compressor 310 can create negative pressure within said debris reservoir 306 via said air nozzle 412. This suction helps draw debris from said grinding surface 404, through said debris channel 402, and into said debris reservoir 306 and the lower tray said lower tray 400.

Said mounting bracket 410 can align and secure said grinding head 300, said drive shaft 408 and said controller 304 along a central axis 416. This bracket ensures that the components are properly aligned for optimal operation.

Said power port 414 can be located on a portion of said outer casing 200 and can allow electrical power to enter said outer casing 200 of said medical waste grinding and separation system 100, and supplying said power system 308. In one embodiment, said power system 308 can comprise a rechargeable battery for portable operation or be directly powered from an external electrical source such as said wall outlet 102.

Figure 5:
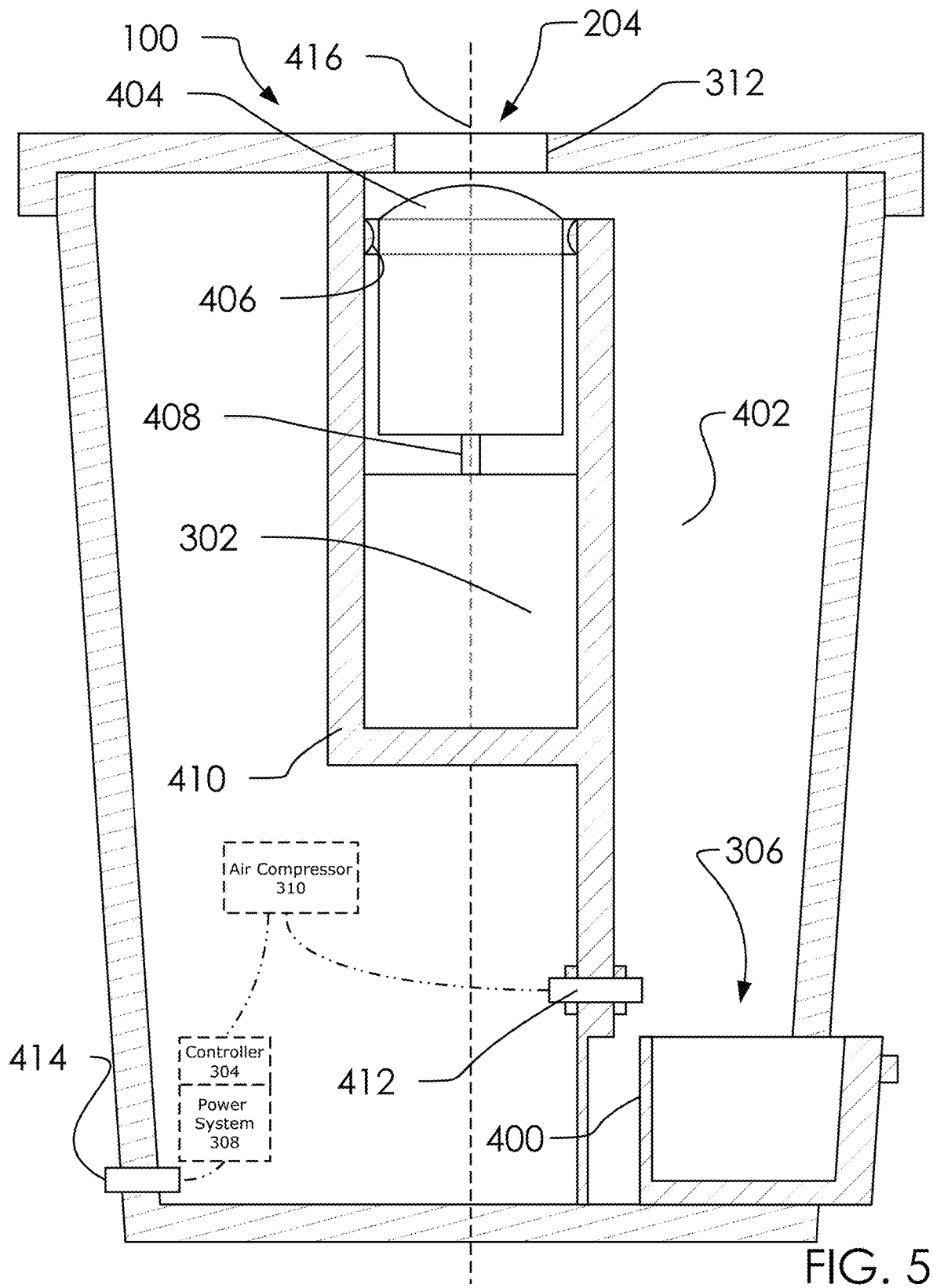
FIG. 5 illustrates an elevated cross-section side view of said medical waste grinding and separation system 100 with a lower tray 400 partially pulled out of a debris reservoir 306.

FIG. 5 illustrates an elevated cross-section side view of said medical waste grinding and separation system 100 with said lower tray 400 partially pulled out of said debris reservoir 306.

Figure 6:
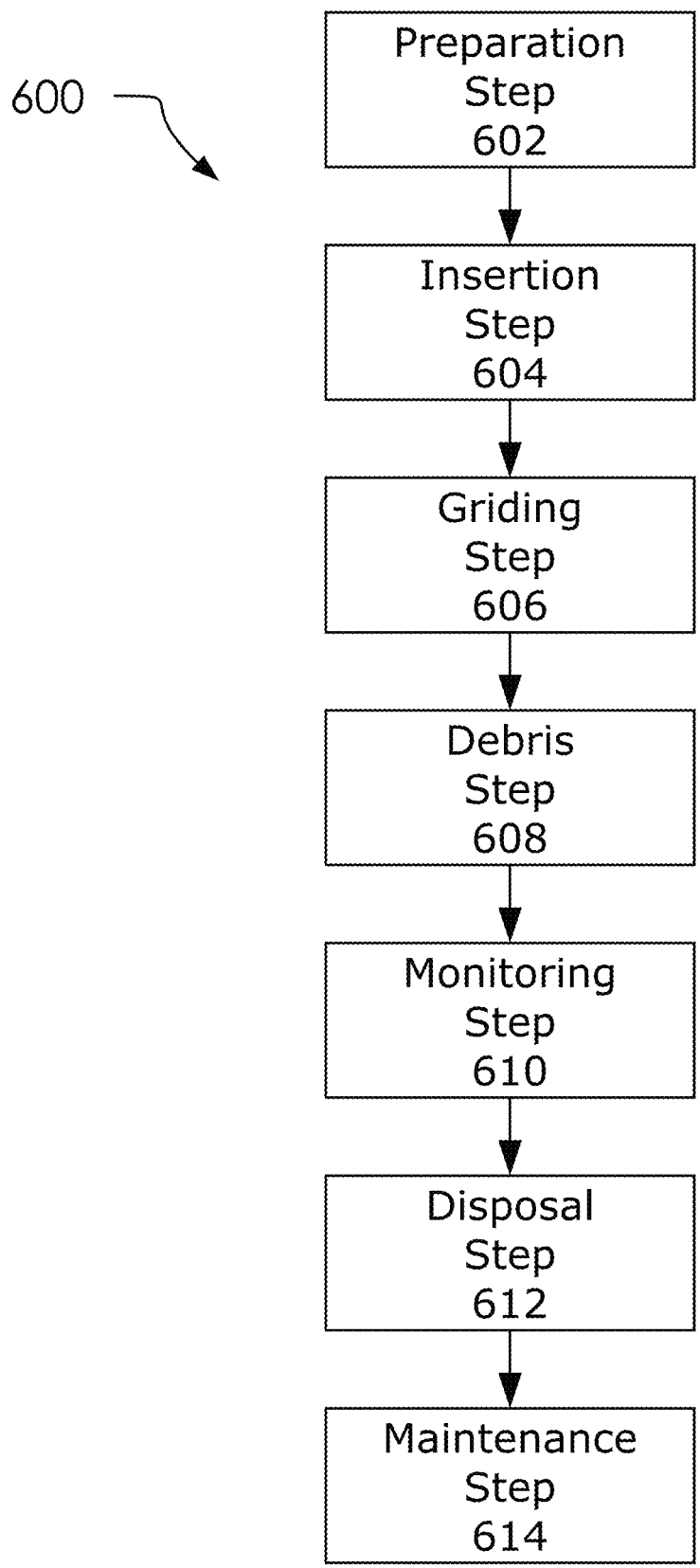
FIG. 6 illustrates a method of use 600 for said medical waste grinding and separation system 100.
Figure 7:
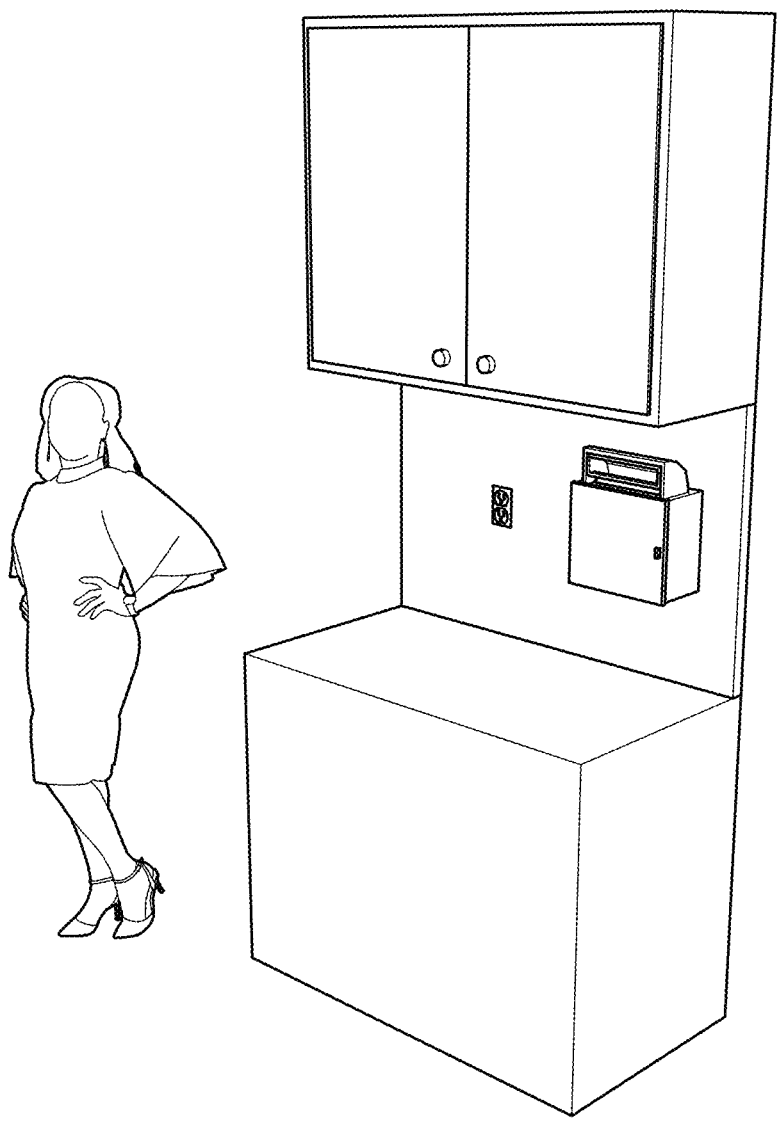
FIGS. 7-10 illustrate four perspective overviews of said medical setting 108 with a wall mount 700 containing said sharps container 106.
Figure 8:
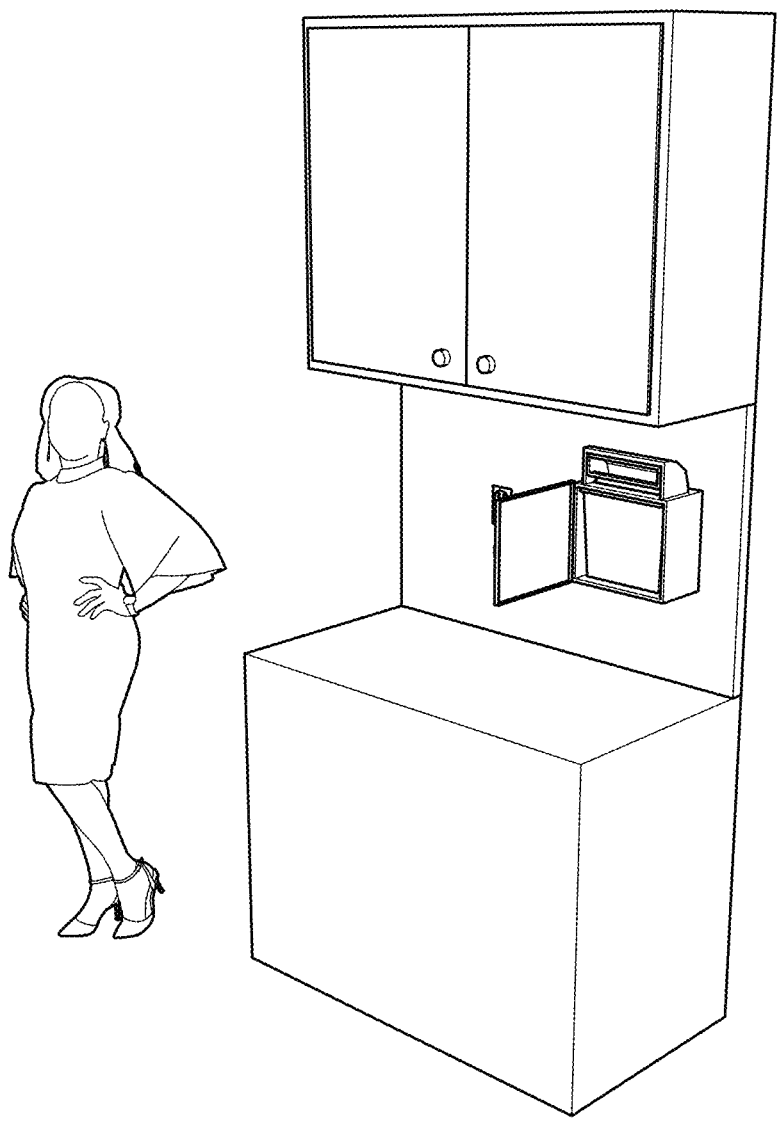
Figure 9:
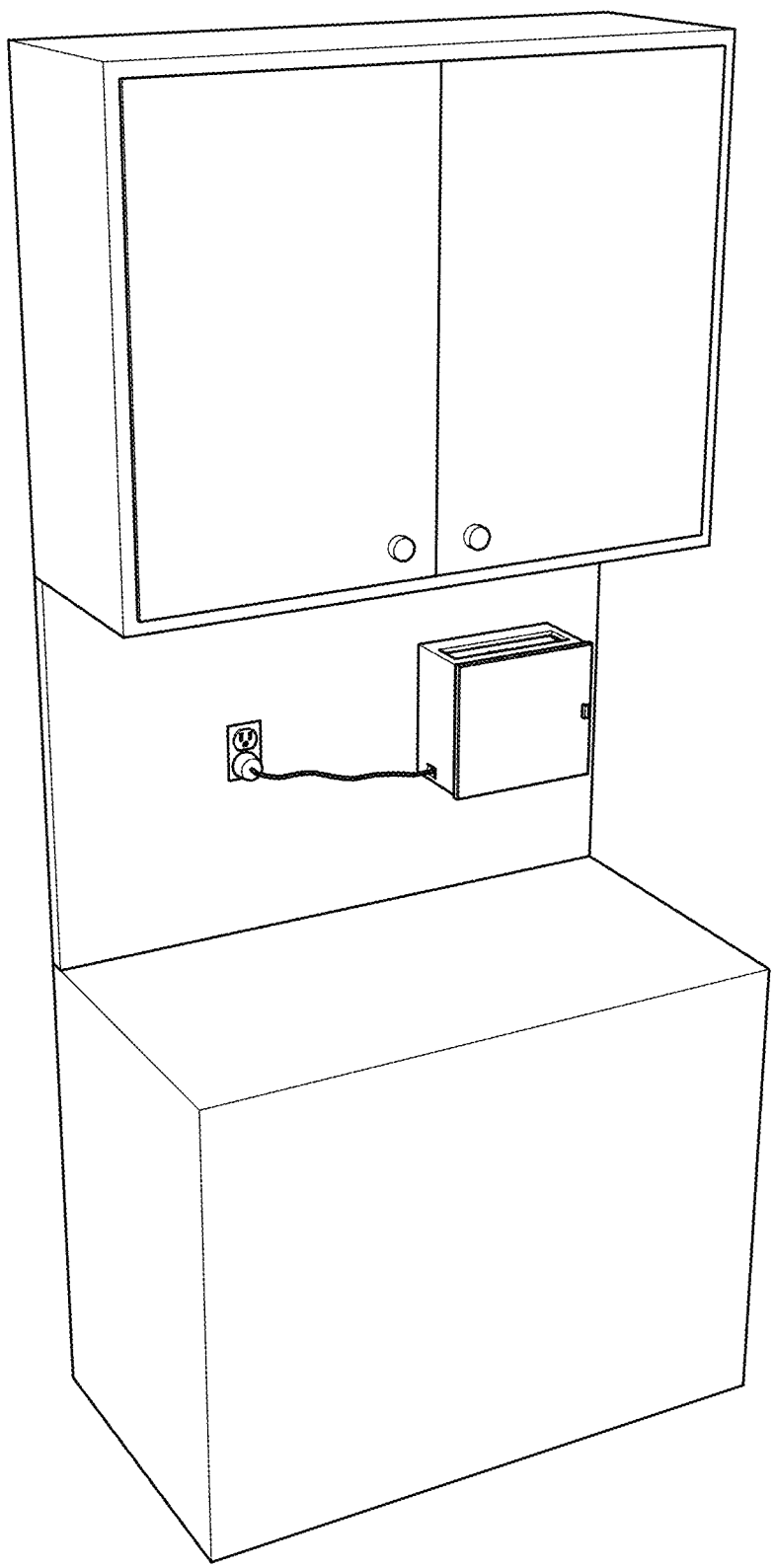
Figure 10:
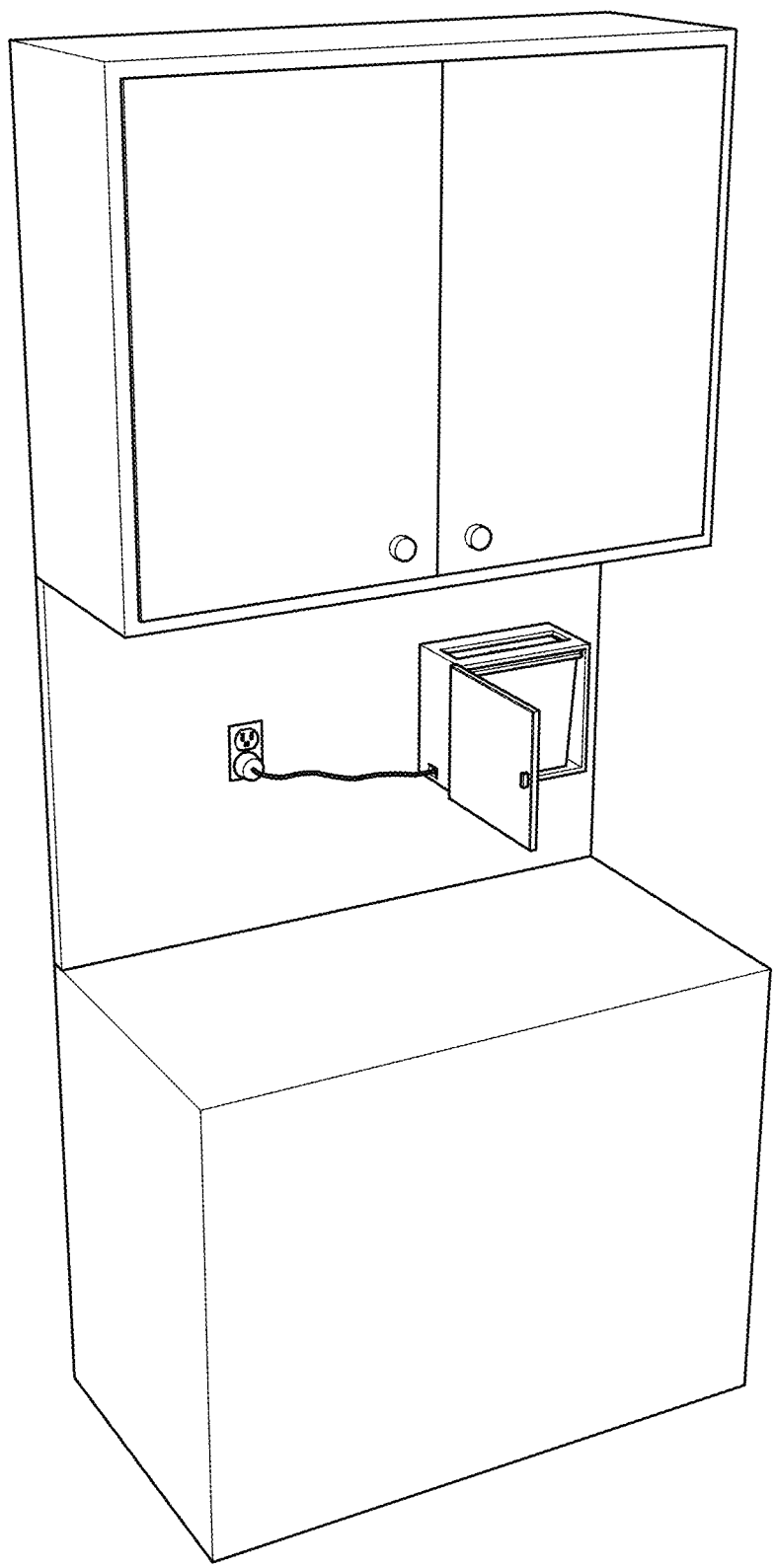

FIG. 6 illustrates a method of use 600 for said medical waste grinding and separation system 100.

In one embodiment, said method of use 600 of said medical waste grinding and separation system 100 can comprise a preparation step 602, an insertion step 604, a grinding step 606, a debris collection step 608, a monitoring step 610, a disposal step 612, and a maintenance step 614.

Wherein, said preparation step 602 can comprise ensuring said medical waste grinding and separation system 100 is properly supplied with power for said power system 308 either with a charged battery or connection to said wall outlet 102; and verifying that said debris reservoir 306 has sufficient space to collect debris.

Said insertion step 604 can comprise inserting contaminated medical sharps or syringe into said sharps aperture 204; and sensing, using said sensor 312, the presence of the object and triggers the activation of said grinding head 300.

Said grinding step 606 can comprise powering said rotary grinding tool motor 302 and driving said grinding head 300 to grind; and controlling, using said controller 304, the grinding process, ensuring optimal operation and safety.

Said debris collection step 608 can comprise directing debris through said debris channel 402 and collecting it in said debris reservoir 306; and generating airflow through said air nozzle 412, creating a negative pressure that helps draw the debris into said debris reservoir 306 and said lower tray 400.

Said monitoring step 610 can comprise monitoring a grinding event using said sensor 312 and said controller 304 and shutting down said rotary grinding tool motor 302 when completed.

Said disposal step 612 can comprise opening said lower tray 400 and removing it from said debris reservoir 306; safely disposing of the collected debris according to medical waste disposal regulations; and reinstalling the cleaned said lower tray 400 into the system.

Finally, said maintenance step 614 can comprise checking and cleaning said sharps aperture 204, said grinding head 300, and said debris reservoir 306 to ensure optimal performance; and recharging a battery, if used, of said power system 308 to ensure continuous connection to a power source as needed.

The flow chart in of said method of use 600 outlines a streamlined process for using the said medical waste grinding and separation system 100. It ensures safe and efficient disposal of medical sharps, protecting healthcare workers and patients from potential hazards associated with handling contaminated medical instruments.

This method of use ensures that the system operates efficiently, maintains hygiene standards, and provides a cost-effective solution for managing medical waste. By following these steps, users can maximize the benefits of the system, ensuring safety and compliance with medical waste disposal regulations.

FIGS. 7-10 illustrate four perspective overviews of said medical setting 108 with a wall mount 700 containing said sharps container 106.

Preferred embodiment as presented in the original claims:

Said medical waste grinding and separation system 100 configured to safely neutralize and dispose of a portion of a medical sharp. Said medical waste grinding and separation system 100 comprises said outer casing 200, said sharps aperture 204, said grinding head 300, said rotary grinding tool motor 302, said debris reservoir 306, said power system 308, said debris channel 402, said drive shaft 408. Said grinding head 300 comprises said grinding surface 404. Said grinding surface 404 comprises a portion of said grinding head 300 being closest to said sharps aperture 204. Said outer casing 200 forms the main structural body of the system, housing the internal components said grinding head 300 and said rotary grinding tool motor 302 can be aligned with one another and said sharps aperture 204. Said grinding head 300 can be configured to grind down the tip of a syringe when it can be inserted into the aperture. Said grinding head 300 can be driven by said rotary grinding tool motor 302. Said debris reservoir 306 comprises a compartment within said medical waste grinding and separation system 100 that collects and stores the ground debris produced by said grinding head 300. Said power system 308 can be configured to provide the necessary electrical power to said medical waste grinding and separation system 100. Said debris channel 402 can be positioned between said sharps aperture 204 and said debris reservoir 306. Said debris channel 402 directs debris from said grinding surface 404 of said grinding head 300 and into said debris reservoir 306. Accordingly, said debris channel 402 ensures that the debris can be efficiently collected without scattering. Said grinding head 300 and said rotary grinding tool motor 302 can be connected via said drive shaft 408. Medical waste grinding and separation system 100 further comprises said air compressor 310, and said air nozzle 412. Said air compressor 310 assists with the collection of debris by generating an airflow that helps direct the ground debris into said debris reservoir 306, maintaining a clean and efficient operation. Said air nozzle 412 can be installed in a portion of said debris reservoir 306 and can be connected to said air compressor 310 to pull air from said debris reservoir 306.

Said medical waste grinding and separation system 100 configured to safely neutralize and dispose of a portion of a medical sharp. Said medical waste grinding and separation system 100 comprises said outer casing 200, said sharps aperture 204, said grinding head 300, said rotary grinding tool motor 302, said debris reservoir 306, said power system 308, said debris channel 402, said drive shaft 408. Said grinding head 300 comprises said grinding surface 404. Said grinding surface 404 comprises a portion of said grinding head 300 being closest to said sharps aperture 204. Said outer casing 200 forms the main structural body of the system, housing the internal components said grinding head 300 and said rotary grinding tool motor 302 can be aligned with one another and said sharps aperture 204. Said grinding head 300 can be configured to grind down the tip of a syringe when it can be inserted into the aperture. Said grinding head 300 can be driven by said rotary grinding tool motor 302. Said debris reservoir 306 comprises a compartment within said medical waste grinding and separation system 100 that collects and stores the ground debris produced by said grinding head 300. Said power system 308 can be configured to provide the necessary electrical power to said medical waste grinding and separation system 100. Said debris channel 402 can be positioned between said sharps aperture 204 and said debris reservoir 306. Said debris channel 402 directs debris from said grinding surface 404 of said grinding head 300 and into said debris reservoir 306. Accordingly, said debris channel 402 ensures that the debris can be efficiently collected without scattering. Said grinding head 300 and said rotary grinding tool motor 302 can be connected via said drive shaft 408. Medical waste grinding and separation system 100 further comprises said air compressor 310, and said air nozzle 412. Said air compressor 310 assists with the collection of debris by generating an airflow that helps direct the ground debris into said debris reservoir 306, maintaining a clean and efficient operation. Said air nozzle 412 can be installed in a portion of said debris reservoir 306 and can be connected to said air compressor 310 to pull air from said debris reservoir 306.

Said medical waste grinding and separation system 100 configured to safely neutralize and dispose of a portion of a medical sharp. Said medical waste grinding and separation system 100 comprises said outer casing 200, said sharps aperture 204, said grinding head 300, said rotary grinding tool motor 302, said debris reservoir 306, said power system 308, said debris channel 402, said drive shaft 408 said grinding head 300 comprises said grinding surface 404. Said grinding surface 404 comprises a portion of said grinding head 300 being closest to said sharps aperture 204. Said outer casing 200 forms the main structural body of the system, housing the internal components said grinding head 300 and said rotary grinding tool motor 302 can be aligned with one another and said sharps aperture 204. Said grinding head 300 can be configured to grind down the tip of a syringe when it can be inserted into the aperture. Said grinding head 300 can be driven by said rotary grinding tool motor 302. Said debris reservoir 306 comprises a compartment within said medical waste grinding and separation system 100 that collects and stores the ground debris produced by said grinding head 300. Said power system 308 can be configured to provide the necessary electrical power to said medical waste grinding and separation system 100. Said debris channel 402 can be positioned between said sharps aperture 204 and said debris reservoir 306. Said debris channel 402 directs debris from said grinding surface 404 of said grinding head 300 and into said debris reservoir 306. Accordingly, said debris channel 402 ensures that the debris can be efficiently collected without scattering. Said grinding head 300 and said rotary grinding tool motor 302 can be connected via said drive shaft 408.

Said controller 304 manages the operation of the various components within said medical waste grinding and separation system 100. Said controller 304 controls said rotary grinding tool motor 302 between active or inactive, as needed for the grinding process. Said controller 304 controls the functions of the other components and maintains the overall operational efficiency and safety of the system.

Medical waste grinding and separation system 100 further comprises said plug 202 attached to said power system 308.

Said power system 308 of said medical waste grinding and separation system 100 comprises a rechargeable battery system for portable operation.

Medical waste grinding and separation system 100 further comprises said air compressor 310, and said air nozzle 412. Said air compressor 310 assists with the collection of debris by generating an airflow that helps direct the ground debris into said debris reservoir 306, maintaining a clean and efficient operation. Said air nozzle 412 can be installed in a portion of said debris reservoir 306 and can be connected to said air compressor 310 to pull air from said debris reservoir 306.

Medical waste grinding and separation system 100 further comprises said sensor 312. Said sensor 312 can be configured to detect the presence of an object inserted into said sharps aperture 204.

Said sensor 312 can be installed in an inner rim of said sharps aperture 204. Based on a signal from said sensor 312, said controller 304 can be configured to trigger the activation of said grinding head 300. Accordingly, said controller 304 can ensure said rotary grinding tool motor 302 drives said grinding head 300 when a medical sharp can be inserted into said sharps aperture 204.

Medical waste grinding and separation system 100 comprises said lower tray 400 selectively inserted into a portion of said debris reservoir 306 and can be removed from said outer casing 200 to discard the collected debris.

Said grinding surface 404 comprises a top portion of said grinding head 300.

Said medical waste grinding and separation system 100 comprises said method of use 600 comprising said preparation step 602, said insertion step 604, said grinding step 606, said debris collection step 608, said monitoring step 610, said disposal step 612 and said maintenance step 614. Said preparation step 602 comprises ensuring said medical waste grinding and separation system 100 can be properly supplied with power for said power system 308 and verifying that said debris reservoir 306 has sufficient space to collect debris. Said insertion step 604 comprises inserting contaminated medical sharp into said sharps aperture 204, and sensing, using said sensor 312, the presence of the object and triggers the activation of said grinding head 300. Said grinding step 606 comprises powering said rotary grinding tool motor 302, driving said grinding head 300 to grind the object, and controlling, using said controller 304, the grinding process, ensuring optimal operation and safety. Said debris collection step 608 comprises directing debris through said debris channel 402, collecting it in said debris reservoir 306, generating airflow through said air nozzle 412, and creating a negative pressure that helps draw the debris into said debris reservoir 306 and said lower tray 400. Said monitoring step 610 comprises monitoring a grinding event using said sensor 312 and said controller 304 and shutting down said rotary grinding tool motor 302 when completed. Said disposal step 612 comprises opening said lower tray 400 and removing it from said debris reservoir 306, safely disposing of the collected debris according to medical waste disposal regulations, and reinstalling the cleaned said lower tray 400 into the system. Said maintenance step 614 comprises checking and cleaning said sharps aperture 204, said grinding head 300, and said debris reservoir 306 to ensure optimal performance. Recharging a battery, if used, of said power system 308 to ensure continuous connection to a power source as needed.

Said method of use 600 of said medical waste grinding and separation system 100 for safely neutralizing and disposing of a portion of a medical sharp. Said method of use 600 comprising ensuring said medical waste grinding and separation system 100 can be properly supplied with power for said power system 308 and verifying that said debris reservoir 306 has sufficient space to collect debris, inserting a contaminated medical sharp into said sharps aperture 204, powering said rotary grinding tool motor 302, driving said grinding head 300 to grind the contaminated medical sharp, directing debris through said debris channel 402, collecting it in said debris reservoir 306, monitoring a grinding event and shutting down said rotary grinding tool motor 302 when completed, safely disposing of the collected debris according to medical waste disposal regulations. Wherein, said medical waste grinding and separation system 100 comprises said outer casing 200, said sharps aperture 204, said grinding head 300, said rotary grinding tool motor 302, said debris reservoir 306, said power system 308, said debris channel 402, said drive shaft 408 said grinding head 300 comprises said grinding surface 404. Said grinding surface 404 comprises a portion of said grinding head 300 being closest to said sharps aperture 204. Said outer casing 200 forms the main structural body of the system, housing the internal components said grinding head 300 and said rotary grinding tool motor 302 can be aligned with one another and said sharps aperture 204. Said grinding head 300 can be configured to grind down the tip of a syringe when it can be inserted into the aperture. Said grinding head 300 can be driven by said rotary grinding tool motor 302. Said debris reservoir 306 comprises a compartment within said medical waste grinding and separation system 100 that collects and stores the ground debris produced by said grinding head 300. Said power system 308 can be configured to provide the necessary electrical power to said medical waste grinding and separation system 100. Said debris channel 402 can be positioned between said sharps aperture 204 and said debris reservoir 306. Said debris channel 402 directs debris from said grinding surface 404 of said grinding head 300 and into said debris reservoir 306. Accordingly, said debris channel 402 ensures that the debris can be efficiently collected without scattering. Said grinding head 300 and said rotary grinding tool motor 302 can be connected via said drive shaft 408.

Said controller 304 manages the operation of the various components within said medical waste grinding and separation system 100. Said controller 304 controls said rotary grinding tool motor 302 between active or inactive, as needed for the grinding process. Said controller 304 controls the functions of the other components and maintains the overall operational efficiency and safety of the system.

Medical waste grinding and separation system 100 further comprises said plug 202 attached to said power system 308.

Said power system 308 of said medical waste grinding and separation system 100 comprises a rechargeable battery system for portable operation.

Medical waste grinding and separation system 100 further comprises said air compressor 310, and said air nozzle 412. Said air compressor 310 assists with the collection of debris by generating an airflow that helps direct the ground debris into said debris reservoir 306, maintaining a clean and efficient operation. Said air nozzle 412 can be installed in a portion of said debris reservoir 306 and can be connected to said air compressor 310 to pull air from said debris reservoir 306.

Medical waste grinding and separation system 100 further comprises said sensor 312. Said sensor 312 can be configured to detect the presence of an object inserted into said sharps aperture 204.

Said sensor 312 can be installed in an inner rim of said sharps aperture 204. Based on a signal from said sensor 312, said controller 304 can be configured to trigger the activation of said grinding head 300. Accordingly, said controller 304 can ensure said rotary grinding tool motor 302 drives said grinding head 300 when a medical sharp can be inserted into said sharps aperture 204.

Medical waste grinding and separation system 100 comprises said lower tray 400 selectively inserted into a portion of said debris reservoir 306 and can be removed from said outer casing 200 to discard the collected debris.

Parts List:
said medical waste grinding and separation system 100,
said medical setting 108,
said wall outlet 102,
said system user 104,
said sharps container 106,
said outer casing 200,
said plug 202,
said sharps aperture 204,
said grinding head 300,
said rotary grinding tool motor 302,
said controller 304,
said debris reservoir 306,
said power system 308,
said air compressor 310,
said sensor 312,
said lower tray 400,
said debris channel 402,
said grinding surface 404,
said blocking element 406,
said drive shaft 408,
said mounting bracket 410,
said air nozzle 412,
said power port 414,
said central axis 416,
said method of use 600,
said preparation step 602,
said insertion step 604,
said grinding step 606,
said debris collection step 608,
said monitoring step 610,
said disposal step 612,
said maintenance step 614, and
said wall mount 700.

Various changes in the details of the illustrated operational methods are possible without departing from the scope of the following claims. Some embodiments may combine the activities described herein as being separate steps. Similarly, one or more of the described steps may be omitted, depending upon the specific operational environment the method is being implemented in. It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein."

The invention claimed is:

1. A medical waste grinding and separation system configured to safely neutralize and dispose of a portion of a medical sharp, wherein:
    said medical waste grinding and separation system comprises an outer casing, a sharps aperture, a grinding head, a rotary grinding tool motor, a debris reservoir, a power system, a debris channel, a drive shaft;
    said grinding head comprises a grinding surface;
    said grinding surface comprises a portion of said grinding head being closest to said sharps aperture;

said outer casing forms the main structural body of the system, housing the internal components
said grinding head and said rotary grinding tool motor is aligned with one another and said sharps aperture;
said grinding head is configured to grind down the tip of a syringe when it is inserted into the aperture;
said grinding head is driven by said rotary grinding tool motor;
said debris reservoir comprises a compartment within said medical waste grinding and separation system that collects and stores the ground debris produced by said grinding head;
said power system is configured to provide the necessary electrical power to said medical waste grinding and separation system;
said debris channel is positioned between said sharps aperture and said debris reservoir;
said debris channel directs debris from said grinding surface of said grinding head and into said debris reservoir;
accordingly, said debris channel ensures that the debris is efficiently collected without scattering;
said grinding head and said rotary grinding tool motor are connected via said drive shaft;
medical waste grinding and separation system 100 further comprises an air compressor, and an air nozzle;
said air compressor assists with the collection of debris by generating an airflow that helps direct the ground debris into said debris reservoir, maintaining a clean and efficient operation; and
said air nozzle is installed in a portion of said debris reservoir and is connected to said air compressor to pull air from said debris reservoir.

2. A medical waste grinding and separation system configured to safely neutralize and dispose of a portion of a medical sharp, wherein:
said medical waste grinding and separation system comprises an outer casing, a sharps aperture, a grinding head, a rotary grinding tool motor, a debris reservoir, a power system, a debris channel, a drive shaft;
said grinding head comprises a grinding surface;
said grinding surface comprises a portion of said grinding head being closest to said sharps aperture;
said outer casing forms the main structural body of the system, housing the internal components
said grinding head and said rotary grinding tool motor is aligned with one another and said sharps aperture;
said grinding head is configured to grind down the tip of a syringe when it is inserted into the aperture;
said grinding head is driven by said rotary grinding tool motor;
said debris reservoir comprises a compartment within said medical waste grinding and separation system that collects and stores the ground debris produced by said grinding head;
said power system is configured to provide the necessary electrical power to said medical waste grinding and separation system;
said debris channel is positioned between said sharps aperture and said debris reservoir;
said debris channel directs debris from said grinding surface of said grinding head and into said debris reservoir;
accordingly, said debris channel ensures that the debris is efficiently collected without scattering; and
said grinding head and said rotary grinding tool motor are connected via said drive shaft.

3. The medical waste grinding and separation system of claim 2, wherein:
a controller manages the operation of the various components within said medical waste grinding and separation system;
said controller controls said rotary grinding tool motor between active or inactive, as needed for the grinding process; and
said controller controls the functions of the other components and maintains the overall operational efficiency and safety of the system.

4. The medical waste grinding and separation system of claim 2, wherein:
said medical waste grinding and separation system further comprises a plug attached to said power system.

5. The medical waste grinding and separation system of claim 2, wherein:
said power system of said medical waste grinding and separation system comprises a rechargeable battery system for portable operation.

6. The medical waste grinding and separation system of claim 2, wherein:
said medical waste grinding and separation system further comprises an air compressor, and an air nozzle;
said air compressor assists with the collection of debris by generating an airflow that helps direct the ground debris into said debris reservoir, maintaining a clean and efficient operation; and
said air nozzle is installed in a portion of said debris reservoir and is connected to said air compressor to pull air from said debris reservoir.

7. The medical waste grinding and separation system of claim 2, wherein:
said medical waste grinding and separation system further comprises a sensor; and
said sensor is configured to detect the presence of an object inserted into said sharps aperture.

8. The medical waste grinding and separation system of claim 7, wherein:
said sensor is installed in an inner rim of said sharps aperture;
based on a signal from said sensor, said controller is configured to trigger the activation of said grinding head; and
accordingly, said controller can ensure said rotary grinding tool motor drives said grinding head when a medical sharp is inserted into said sharps aperture.

9. The medical waste grinding and separation system of claim 2, wherein:
said medical waste grinding and separation system comprises a lower tray selectively inserted into a portion of said debris reservoir and can be removed from said outer casing to discard the collected debris.

10. The medical waste grinding and separation system of claim 2, wherein:
said grinding surface comprises a top portion of said grinding head.

11. The medical waste grinding and separation system of claim 2, wherein:
said medical waste grinding and separation system comprises a method of use comprising a preparation step, an insertion step, a grinding step, a debris collection step, a monitoring step, a disposal step and a maintenance step;
said preparation step comprises ensuring said medical waste grinding and separation system is properly supplied with power for said power system and verifying that said debris reservoir has sufficient space to collect debris;

said insertion step comprises inserting contaminated medical sharp into said sharps aperture, and sensing, using said sensor, the presence of the object and triggers the activation of said grinding head;

said grinding step comprises powering said rotary grinding tool motor, driving said grinding head to grind the object, and controlling, using said controller, the grinding process, ensuring optimal operation and safety;

said debris collection step comprises directing debris through said debris channel, collecting it in said debris reservoir, generating airflow through said air nozzle, and creating a negative pressure that helps draw the debris into said debris reservoir and said lower tray;

said monitoring step comprises monitoring a grinding event using said sensor and said controller and shutting down said rotary grinding tool motor when completed;

said disposal step comprises opening said lower tray and removing it from said debris reservoir, safely disposing of the collected debris according to medical waste disposal regulations, and reinstalling the cleaned said lower tray into the system; and said maintenance step comprises checking and cleaning said sharps aperture, said grinding head, and said debris reservoir to ensure optimal performance; and recharging a battery, if used, of said power system to ensure continuous connection to a power source as needed.

12. A method of use of a medical waste grinding and separation system for safely neutralizing and disposing of a portion of a medical sharp, wherein:

said method of use comprising ensuring said medical waste grinding and separation system is properly supplied with power for a power system, verifying that a debris reservoir has sufficient space to collect debris, inserting a contaminated medical sharp into a sharps aperture, powering a rotary grinding tool motor, driving a grinding head to grind the contaminated medical sharp, directing debris through a debris channel, collecting it in said debris reservoir, monitoring a grinding event and shutting down said rotary grinding tool motor when completed, and safely disposing of the collected debris according to medical waste disposal regulations; wherein, said medical waste grinding and separation system comprises an outer casing, said sharps aperture, said grinding head, said rotary grinding tool motor, said debris reservoir, said power system, said debris channel, a drive shaft said grinding head comprises a grinding surface;

said grinding surface comprises a portion of said grinding head being closest to said sharps aperture;

said outer casing forms the main structural body of the system, housing the internal components said grinding head and said rotary grinding tool motor is aligned with one another and said sharps aperture;

said grinding head is configured to grind down the tip of a syringe when it is inserted into the aperture;

said grinding head is driven by said rotary grinding tool motor;

said debris reservoir comprises a compartment within said medical waste grinding and separation system that collects and stores the ground debris produced by said grinding head;

said power system is configured to provide the necessary electrical power to said medical waste grinding and separation system;

said debris channel is positioned between said sharps aperture and said debris reservoir;

said debris channel directs debris from said grinding surface of said grinding head and into said debris reservoir;

accordingly, said debris channel ensures that the debris is efficiently collected without scattering; and said grinding head and said rotary grinding tool motor are connected via said drive shaft.

13. The medical waste grinding and separation system of claim 2, wherein:

said controller manages the operation of the various components within said medical waste grinding and separation system;

said controller controls said rotary grinding tool motor between active or inactive, as needed for the grinding process; and said controller controls the functions of the other components and maintains the overall operational efficiency and safety of the system.

14. The medical waste grinding and separation system of claim 2, wherein:

medical waste grinding and separation system further comprises said plug attached to said power system.

15. The medical waste grinding and separation system of claim 2, wherein:

said power system of said medical waste grinding and separation system comprises a rechargeable battery system for portable operation.

16. The medical waste grinding and separation system of claim 2, wherein:

medical waste grinding and separation system further comprises said air compressor, and said air nozzle;

said air compressor assists with the collection of debris by generating an airflow that helps direct the ground debris into said debris reservoir, maintaining a clean and efficient operation; and said air nozzle is installed in a portion of said debris reservoir and is connected to said air compressor to pull air from said debris reservoir.

17. The medical waste grinding and separation system of claim 2, wherein:

medical waste grinding and separation system further comprises said sensor; and said sensor is configured to detect the presence of an object inserted into said sharps aperture.

18. The medical waste grinding and separation system of claim 17, wherein:

said sensor is installed in an inner rim of said sharps aperture;

based on a signal from said sensor, said controller is configured to trigger the activation of said grinding head; and accordingly, said controller can ensure said rotary grinding tool motor drives said grinding head when a medical sharp is inserted into said sharps aperture.

19. The medical waste grinding and separation system of claim 2, wherein:

said medical waste grinding and separation system comprises said lower tray selectively inserted into a portion of said debris reservoir and can be removed from said outer casing to discard the collected debris.

20. The medical waste grinding and separation system of claim 2, wherein:

said grinding surface comprises a top portion of said grinding head.

* * * * *